(12) United States Patent
Cumming

(10) Patent No.: US 8,523,942 B2
(45) Date of Patent: Sep. 3, 2013

(54) VARIABLE FOCUS INTRAOCULAR LENS

(76) Inventor: James Stuart Cumming, Laguna Beach, CA (US)

( * ) Notice: Subject to any disclaimer, the term of this patent is extended or adjusted under 35 U.S.C. 154(b) by 0 days.

(21) Appl. No.: 13/472,354

(22) Filed: May 15, 2012

(65) Prior Publication Data

US 2012/0296425 A1    Nov. 22, 2012

Related U.S. Application Data

(60) Provisional application No. 61/519,103, filed on May 17, 2011.

(51) Int. Cl.
*A61F 2/16* (2006.01)

(52) U.S. Cl.
USPC .................. 623/6.46; 623/6.37; 623/6.44

(58) Field of Classification Search
USPC ............... 623/6.37, 6.38, 6.43, 6.44, 6.46, 623/6.47, 6.49, 6.4, 6.45
See application file for complete search history.

(56) References Cited

U.S. PATENT DOCUMENTS

| | | | | |
|---|---|---|---|---|
| 5,843,187 | A * | 12/1998 | Bayers | 623/6.46 |
| 6,660,035 | B1 * | 12/2003 | Lang et al. | 623/6.37 |
| 7,229,476 | B2 * | 6/2007 | Azar | 623/6.26 |
| 8,216,308 | B2 * | 7/2012 | Blake et al. | 623/6.37 |
| 2006/0064162 | A1 * | 3/2006 | Klima | 623/6.37 |
| 2013/0073039 | A1 * | 3/2013 | Mirlay | 623/6.38 |

* cited by examiner

*Primary Examiner* — David H Willse
*Assistant Examiner* — Javier Blanco
(74) *Attorney, Agent, or Firm* — Kainoa Asuega; One LLP

(57) ABSTRACT

A variable focus intraocular lens comprises an optic coupled to at least one haptic at a flexion that sets a non-zero angle between the optic and the haptic.

5 Claims, 5 Drawing Sheets

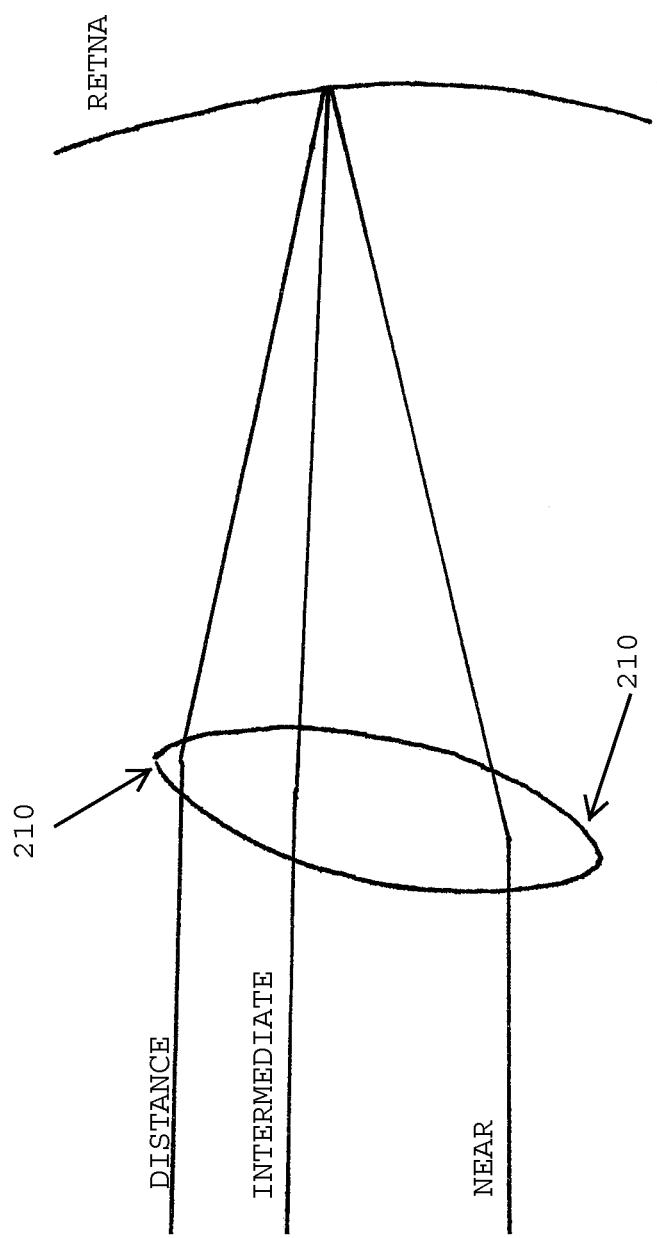

VARIABLE FOCUS INTRAOCULAR LENS

CROSS-REFERENCE TO RELATED APPLICATIONS

This application is based on U.S. Provisional Application No. 61/519,103, filed on May 17, 2011, the contents and disclosures of which are fully incorporated herein by reference.

BACKGROUND OF THE INVENTION

Premium intraocular lenses commonly implanted during cataract surgery are categorized in three ways: accommodating, multifocal and toric intraocular lenses The best visual acuity is achieved with the single focus accommodating lenses. The optic of these lenses moves forward and backward upon constriction and relaxation of the ciliary muscle. However, for reading in dim lighting conditions, or for small print, weak reading glasses are often necessary.

Multifocal lenses focus light on the retina at either two or three focal lengths. Thus, there is more than one image on the retina simultaneously forcing patients to select the image they wish to perceive, which poses a problem for patients unable to adjust their focal point. This creates additional problems in that the amount of light in focus is divided between the multiple focal points, and contrast sensitivity is thereby reduced, making vision at all distances difficult in dim lighting. In addition, there are severe problems when driving at night when the pupil is dilated. Many patients experience severe glare and halos and many have had to have the multifocal lenses explanted and replaced with a single vision standard lens, because of this problem. However, the near vision with the multifocal lenses is superior to that of the current accommodating lens.

Toric lenses correct eyes that have significant astigmatism.

The currently marketed plate accommodating intraocular lenses provide excellent distance and intermediate vision but sometimes require weak, +1.00, reading glasses for prolonged reading, for seeing small print, or reading in dim lighting conditions.

It is desirable to provide a single vision intraocular lens that will allow seamless vision at all distances. However, without excellent uncorrected distance vision there is no point in implanting lenses designed to give seamless vision from far to near.

Furthermore, it is important for intraocular lenses to have a consistent location along the axis of the eye to provide good uncorrected distance vision and to center in the middle of the vertical meridian of the eye.

The original intraocular lens consisted of a single optic. These lenses frequently de-centered and dislocated and it was discovered that there was a need to center and fixate the lens optic in the vertical meridian of the eye.

Attachments to the optic that center and fixate the lens within the capsular bag are called haptics. Traditionally, haptics consist of multiple flexible loops of various designs, J loops, C loops, closed loops and flexible radial arms. Recently, traditional haptics have been replaced in some lens designs with oblong, flat flexible plates, called plate haptics. These plate haptics usually made from silicone, are solid, flat, flexible and between 3.0 and 6.0 mm in width, 0.20 to 0.75 mm thick, and may have tapered, rounded or parallel sides. Plate haptics often have flexible loops or fingers that help center and fixate the lens within the capsular bag. These flexible fingers extend beyond the distal or outer end of the plate haptics and slightly beyond the diameter of the capsular bag and are designed to flex centrally to center and fixate the lens and its optic within the capsular bag.

An intraocular lens (IOL) is a lens implanted into the eye, usually replacing a normal human lens that has been clouded over by a cataract, or can replace a normal human lens as a form of refractive surgery to change the eye's optical power.

An accommodating IOL (AIOL) permits refocusing by means of movement along the optical axis in response to the constriction or relaxation of ciliary muscles. Near vision results from a forward movement of the optic on constriction of the ciliary muscle, which causes an increase in the pressure in the posterior part of the eye with a simultaneous decrease in pressure in the anterior part of the eye. Distance vision results from the reverse pressure change that takes place upon relaxation of the ciliary muscle and the resultant backwards movement of the lens. The movement of the optic enables the patient implanted with the lens to automatically change their vision between far, intermediate and near.

IOLs are known to consist of opposing haptics positioned on either side of a lens optic. Once a patient's cataract is removed, by e.g. phacoemulsification, the IOL is placed into the capsular bag. The haptics help to center the IOL and fixate it within the capsular bag by fibrosis. Such AIOLs are described in U.S. Pat. Nos. 5,674,282, 5,476,514, and U.S. Pat. No. 5,496,366, to Cumming, herein incorporated by reference in its entirety.

Current IOL solutions suffer from the disadvantages identified above.

SUMMARY OF THE INVENTION

An accommodating intraocular lens according to an embodiment of the present invention is described that overcomes the deficiencies of present designs noted above.

The field of the invention is a single focus intraocular lens that provides seamless vision from distance to near without glare or halos.

An intraocular lens is provided wherein an optic is coupled to at least one haptic at a flexion, the flexion setting a non-zero angle between the optic and the haptic.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawing(s) is at least one of the best mode embodiments of the present invention In such drawing(s):

FIG. 3 is a schematic view of an optic tilted according to at least one embodiment of the present invention;

DETAILED DESCRIPTION OF THE PREFERRED EMBODIMENTS

The above described drawing figures illustrate the described invention in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present invention.

A preferred embodiment will now be described with reference to FIGS. 1A and 1B.

An intraocular lens (IOL) 100 comprises: an optic 200 coupled to at least one haptic 300 at a flexion 342 that sets a non-zero angle between the optic 200 and the at least one haptic 300.

The IOL 100 is placed into the capsular bag of a patient's eye after cataract surgery via known techniques such as, for example, phacoemulsification. The lens is centered so that the optical axis of the lens coincides with that of the patient's eye. The haptics 300 contact the capsular bag and the natural fibrosis of the tissue secures the haptics 300, and consequently the IOL 100, in place. Because of the non-zero angle, the IOL provides seamless near to distance vision.

The optic 200 is preferably a single focus optic that gathers the incoming light and focuses it on the retina of the patient so as to effect vision. The optic 200 may be bioconvex, refractive, diffractive, plano-convex, Fresnell, spheric, aspheric, toric, or of any other type that is substantially single focus. In order to permit the optic 200 to be inserted into the eye through a small incision, the optic 200 is preferably made of a flexible optical material, such as, for example, silicone, acrylic, hydrogel, or other flexible optical material now known or hereafter developed. Additionally, the optic may contain a UV blocker.

Figure 1B:
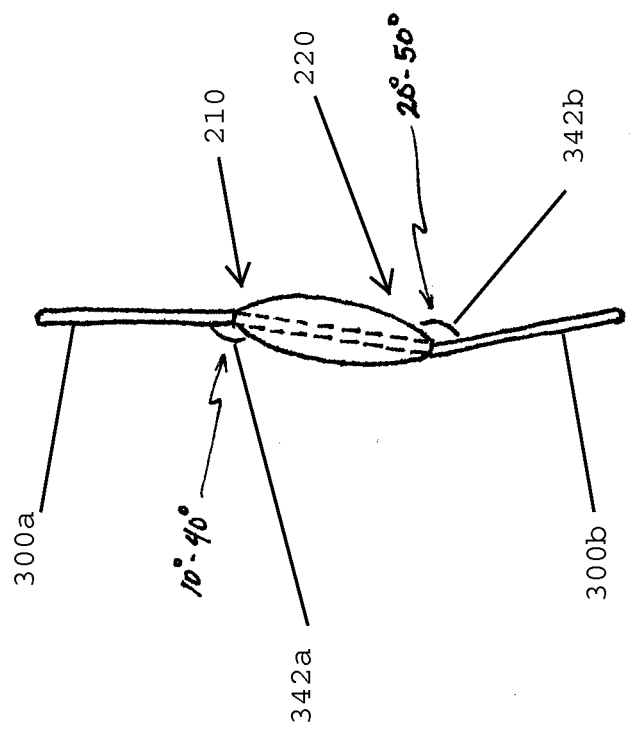
FIGS. 1A and 1B are a top plan view and a side plan view, respectively, of an IOL according to at least one embodiment of the present invention.
Figure 1A:
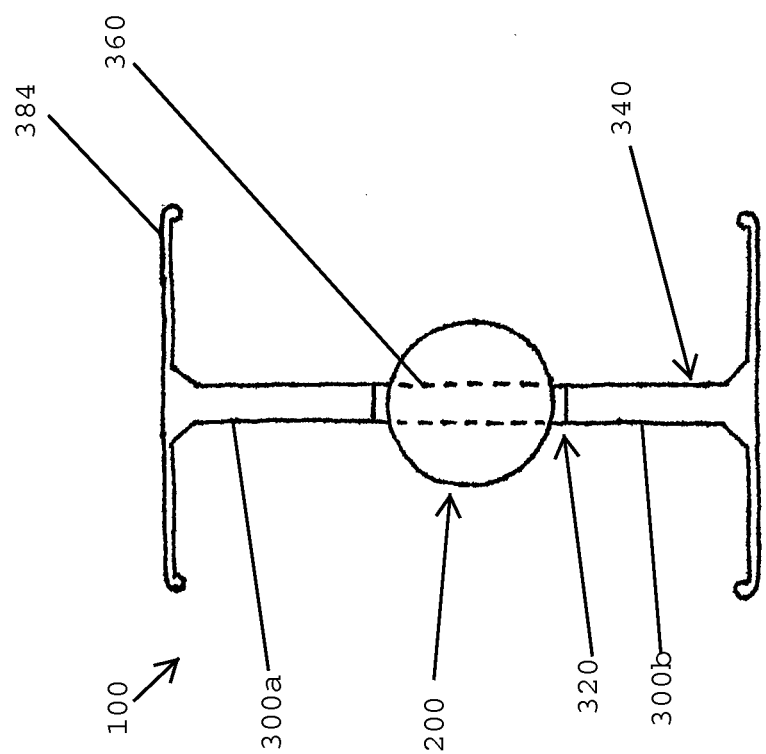
Figure 2:
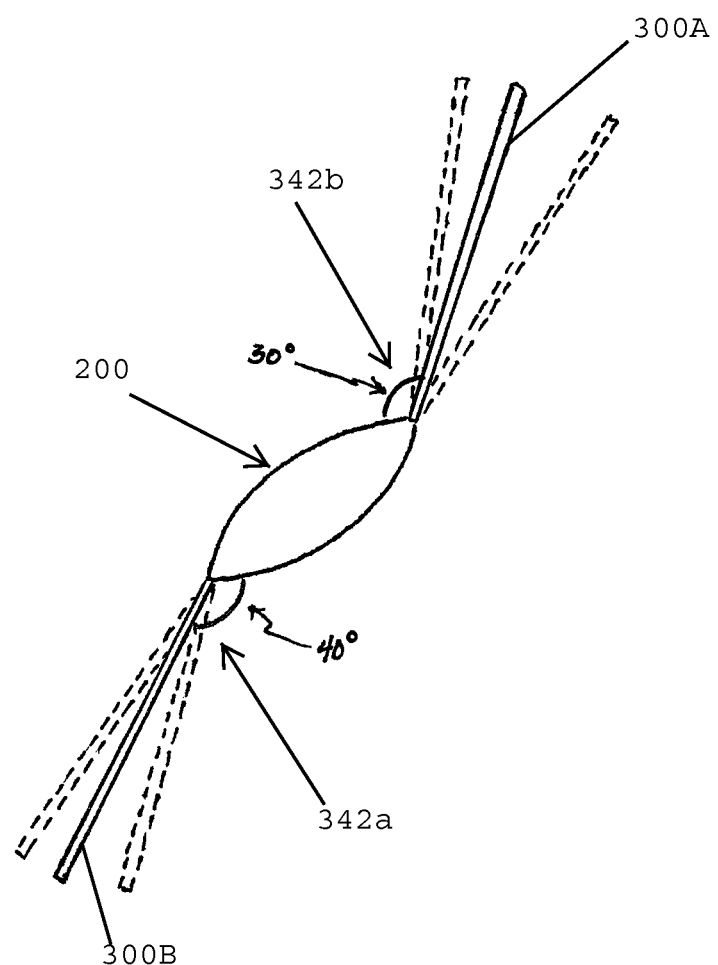
FIG. 2 is a side plan view of an IOL having flexions according to at least one embodiment of the present invention.

As shown in FIGS. 1A and 1B, the optic 200 is coupled to at least one haptic 300 having distal 320 and proximal 340 ends. Flexion 342 substantially biases the optic 200 with respect to the distal end 320 of the haptic 300, and comprises the proximal end 340 set at a non-straight angle with respect to the distal end 320.

In a preferred embodiment, the IOL comprises opposing first and second haptics 300a and 300b. Flexion 342a biases a superior hemisphere 210 of the optic 200 substantially anteriorly with respect to distal end 320a and sets an angle between proximal 340a and distal 320a ends. Flexion 342b biases an inferior hemisphere 220 of the optic 200 posteriorly with respect to the distal end 320b and sets an angle between the proximal 340b and distal 320b ends. Thus, as seen in FIG. 1A, the profile of the IOL 100 resembles a stretched out "Z" resulting in a tilted optic. And, as show in FIG. 3, this stretched out "Z" shape permits the anteriorly biased portion of the lens (i.e. the inferior hemisphere 220) to focus light for near vision, and the posteriorly biased portion of the lens (i.e. the superior hemisphere 210) to focus light for far vision. The lens optic will thus focus objects from distance to near seamlessly. In at least one embodiment, each flexion 342a and 342b is preferably at an angle that is not less than 10 degrees and not more than 50 degrees. Preferably, anterior flexion 342a is at an angle from approximately 10 degrees to approximately 40 degrees, while posterior flexion 342b is at an angle from approximately 20 degrees to approximately 50 degrees.

In at least one embodiment, the IOL is place within the capsular bag with the anterior flexion 342a located at a twelve o'clock position in the eye, and the posterior flexion 342b located at a six o'clock position of the eye. In this manner, the inferior hemisphere 220 of the optic lies forward of the superior hemisphere 210 and focuses light for near vision, while the superior hemisphere 210 of the optic lies rearward of the inferior hemisphere 220 and focuses light for distance vision. The afore mentioned orientation mimics the orientation of external bifocals for convenience of the patient, but a reverse orientation may also be utilized.

Turning to FIG. 1A, a central element 360 may extend through the center of the optic 200 and protrude slightly on opposing sides thereof and couple the optic 200 to opposing haptics 300a and 300b. In some embodiments, the central element 360 and opposing haptics 300 may comprise one contiguous structure, the central element 360 of which passes through the center of the optic 200. In a preferred embodiment, the central element 360 comprises a flat rigid piece over which is molded the flexible optic 200. In order to maintain optical integrity, it is preferable that the central element 360 have a refractive index that is the same or substantially similar to the optic 200. Preferably, the central element is made of the same or similar, flexible, semi-rigid or substantially non-flexible material, as the haptics 300, including but not limited to: acrylic, PMMA, polycarbonate, nylon, or similar clear optical material.

Turning now to FIG. 1B, the at least one haptic 300 is preferably a substantially rigid plate haptic 300 having distal 320 and proximal 340 ends angularly set so as to form flexion 342. The rigid plate haptic 300 operates to engage, fixate and center the haptic into the capsular bag. The haptic may be such as to enable insertion into the eye via a small incision. In at least one embodiment, the plate haptic is between 2.0 mm to 5.0 mm wide and between 9.0 mm to 11.0 mm long. It is preferable that the haptic body be constructed of the same or similar flexible or semi-rigid material as the optic, including, but not limited to: silicone, hydrogel, acrylic, or similar material.

Flexible projections 384, or fingers, may extend from the distal end 320 to engage the capsular bag and secure and center the IOL 100 thereto. The projections 384 may be homogeneous and may be made of either polyimide, PMMA, acrylic or any other inert material.

Figure 4B:
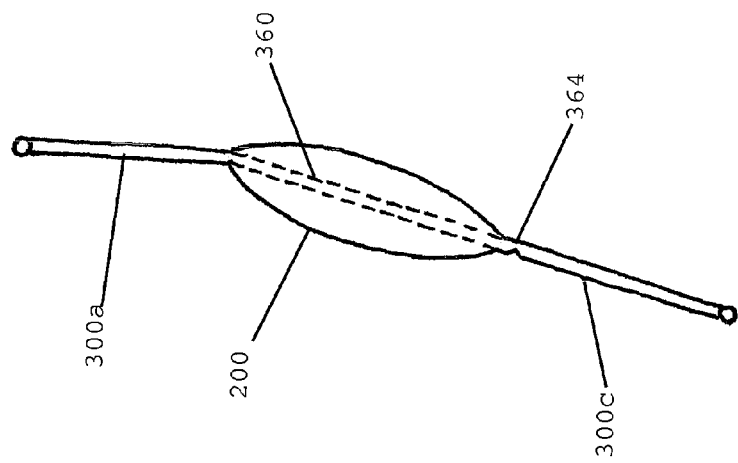
FIGS. 4A and 4B are a top plan view and a side plan view, respectively, of an IOL according to at least one embodiment of the present invention.
Figure 4A:
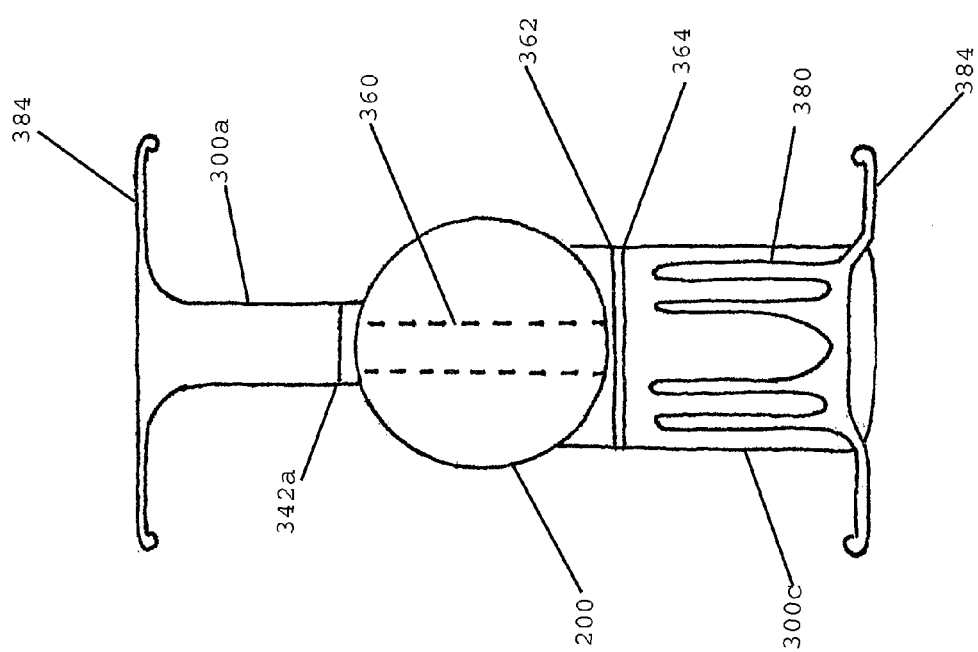
Figure 5A:
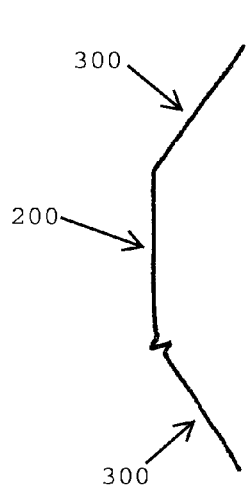
FIG. 5 is a progression side plan view plan view of an IOL according to at least one embodiment of the present invention.
Figure 5B:
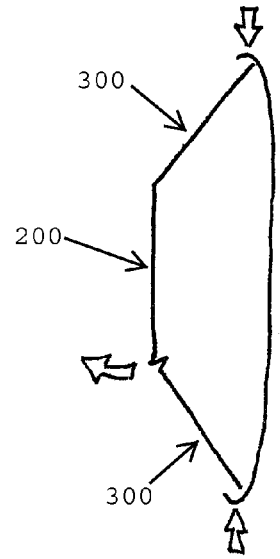
Figure 5C:
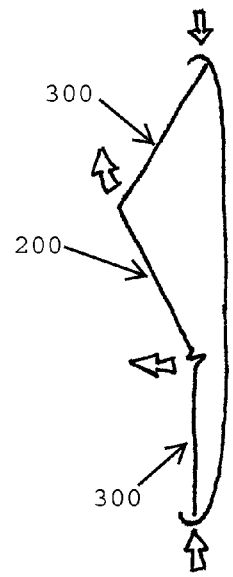
Figure 5D:
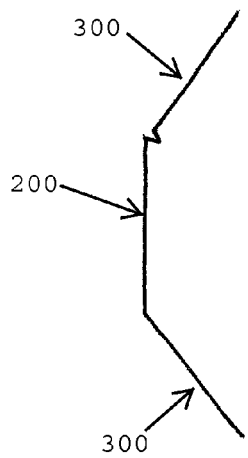
Figure 5E:
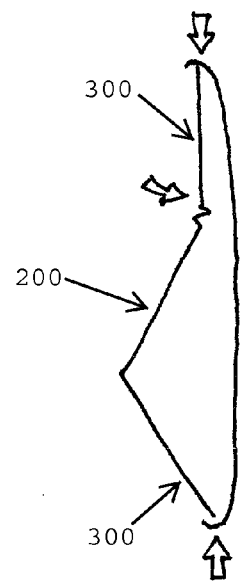
Figure 5F:
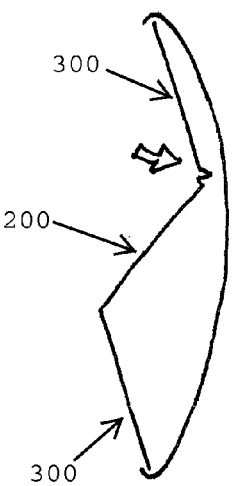

Turning to FIG. 4, in at least one embodiment, the optic 200 is coupled to a substantially rigid plate haptic 300a and a semi-flexible plate haptic 300c. Plate haptic 300a has distal 320 and proximal 340 ends angularly set so as to form flexion 342, as discussed herein, and is coupled to central element 360 extending through the optic 200. Plate haptic 300c is operable to permit accommodation of the associated portion of the IOL and is be coupled to the optic 200 via a flexible connecting member 362 made of the same or similar flexible material as the optic 200.

The connecting member 362 may comprise a hinge 364 extending transversely across either or both sides that is an area of the connecting member 362 that operates to weaken the connecting member 362 so that vitreous pressure can stretch the base of the hinge 364 like an elastic band to allow the optic 200 to move forward. In this manner, the IOL is able to partially accommodate according to the semi-flexible plate haptic 300c and is also able to provide seamless distance to near vision.

The semi-flexible plate haptic 300c operates to engage, fixate and center the haptic into the capsular bag so as to move centrally and posteriorly in response to ciliary muscle flexion, as shown in FIG. 5, such movement, combined with the change in vitreous pressure and end-to-end compression of the distal ends 340 of the haptics 300 via contraction of the ciliary muscles, causing the associated hemisphere of the optic 200 to move forward.

The haptic 300c may be substantially flexible in the transverse direction and substantially rigid in the longitudinal direction so as to enable folded insertion into the eye via a small incision. A frame 380 may be embedded within the haptic body so as to promote the longitudinal rigidity thereof. The frame 380 may be formed of polyimide, prolene, polymethylmethanylate (PMMA), titanium, or similar material. One of ordinary skill will appreciate that while substantial rigidity may promote vaulting; the degree of rigidity imposed is not intended to preclude an effective vault of the optic at the connecting member 362. It is preferable that the haptic be constructed of the same or similar flexible or semi-rigid material as the optic, including, but not limited to: silicone, hydrogel, acrylic, or similar material.

As shown in FIG. 4, the frame 380 may be integral with projections 384, or fingers, that extend from the distal end 320 to engage the capsular bag and secure and center the IOL 100 thereto. The projections 384 may be homogeneous and may be made of either polyimide, PMMA, acrylic or any other inert material.

Exemplary semi-flexible plate haptics are described in U.S. patent Ser. Nos. 13/017,189; 13/092,359; 13/111,599; and 13/155,327, incorporated herein by reference in their entireties.

In at least one embodiment, the longitudinal length of the IOL (i.e. from distal end to distal end) may be between approximately 9.0-11.0 mm, with the diameter as measured from the tips of the lateral projections being between approximately 11.5-12.0 mm. The haptics 300 are preferably between 2.0-6.0 mm wide and 0.20-0.75 mm thick, while the optic may be approximately 4.5-6.0 mm in diameter.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that the named inventor believes that the claimed subject matter is what is intended to be patented.

What is claimed is:

1. A variable focus intraocular lens (IOL) adapted to be placed into the capsular bag of a patient's eye after cataract surgery, said intraocular lens comprising:
    a first plate haptic and an opposite second plate haptic, each of said opposing first and second haptics having a distal end and a proximal end,
    a single focus optic comprising a superior hemisphere, an inferior hemisphere, and a substantially rigid central element extending through the center of the optic, said central element protruding slightly on opposing sides of the optic and coupling the optic to said opposing first and second haptics at first and second flexions, respectively,
    wherein the central element has substantially the same refractive index as the optic,
    wherein the superior hemisphere is adapted to be positioned at the twelve o'clock in the eye, and the inferior hemisphere is adapted to be positioned at the six o'clock position in the eye,
    wherein the first flexion biases the superior hemisphere of the optic substantially posteriorly and sets an angle of approximately 10 degrees to approximately 40 degrees between the optic and the first plate haptic, wherein the second flexion biases the inferior hemisphere of the optic substantially anteriorly and sets an angle of approximately 20 degrees to approximately 50 degrees between the optic and the second plate haptic, and wherein the profile of the IOL resembles a stretched out "Z" resulting in a tilted optic.

2. The intraocular lens of claim 1, wherein the optic is molded over the central element.

3. The intraocular lens of claim 1, further comprising:
    a flexible connecting member, wherein the flexible connecting member permits movement of said inferior hemisphere of the optic between an anterior position and a posterior position.

4. The intraocular lens of claim 1, further comprising projections extending laterally from the distal ends of said first and second haptics so as to engage a capsular bag when the intraocular lens is inserted into an eye.

5. The intraocular lens of claim 1, wherein the first and second haptics and the optic are made of the same material.

* * * * *